(12) United States Patent
Volkmer et al.

(10) Patent No.: US 10,758,295 B2
(45) Date of Patent: Sep. 1, 2020

(54) MICROSURGICAL INSTRUMENT, HANDLE AND ENGINE BLOCK FOR A MICROSURGICAL INSTRUMENT

(71) Applicant: Karl Storz SE & Co. KG, Tuttlingen (DE)

(72) Inventors: Dominik Volkmer, Fridlingen (DE); Jochen Stefan, Wald (DE); Yann Thouément, Les Essarts le Roi (FR); Régis Besse, Guyancourt (FR)

(73) Assignee: Karl Storz SE & Co. KG, Tuttlingen (DE)

( * ) Notice: Subject to any disclaimer, the term of this patent is extended or adjusted under 35 U.S.C. 154(b) by 569 days.

(21) Appl. No.: 15/298,594

(22) Filed: Oct. 20, 2016

(65) Prior Publication Data

US 2017/0112566 A1   Apr. 27, 2017

(30) Foreign Application Priority Data

Oct. 21, 2015 (DE) ........................ 10 2015 013 923

(51) Int. Cl.
   *A61B 18/14*   (2006.01)
   *A61B 17/29*   (2006.01)
   (Continued)

(52) U.S. Cl.
   CPC .... *A61B 18/1445* (2013.01); *A61B 17/00234* (2013.01); *A61B 17/29* (2013.01);
   (Continued)

(58) Field of Classification Search
   CPC ................ A61B 17/29; A61B 17/2909; A61B 2017/2919; A61B 2017/00017;
   (Continued)

(56) References Cited

U.S. PATENT DOCUMENTS

| 5,480,409 A * | 1/1996 | Riza ................... A61B 17/2909 606/205 |
| 2006/0178672 A1* | 8/2006 | Shores ............... A61B 17/1633 606/79 |

(Continued)

FOREIGN PATENT DOCUMENTS

| DE | 19722062 A1 | 12/1998 |
| EP | 1915966 A1 | 4/2008 |

(Continued)

OTHER PUBLICATIONS

European Search Report Application No. EP 16 00 2251 Completed: Dec. 15, 2016;dated Dec. 23, 2016 8 pages.

*Primary Examiner* — Eun Hwa Kim
*Assistant Examiner* — Adam Z Minchella
(74) *Attorney, Agent, or Firm* — Whitmyer IP Group LLC

(57) ABSTRACT

A microsurgical instrument, with a handle and a removably insertable engine block. The handle can be coupled with a work piece and includes a base body and, mounted in the base body, an input shaft for motorized actuation of at least one degree of freedom of the work piece. In addition, the handle has an engine interface, into which the engine block can be installed, and on which at least an electric contact and a mechanical coupling are situated, the mechanical coupling includes a claw coupling element that is non-rotatably connected with the input shaft and can be coupled with a corresponding claw coupling element of the engine block. In addition, the handle has an actuation element, with which a current flow through the electric contact of the engine interface can be activated and deactivated. The claw coupling element of the handle is mounted on the input shaft so that it can slide longitudinally.

19 Claims, 4 Drawing Sheets

(51) Int. Cl.
*A61B 17/00* (2006.01)
*A61B 18/00* (2006.01)

(52) U.S. Cl.
CPC ...... *A61B 17/2909* (2013.01); *A61B 18/1482* (2013.01); *A61B 2017/003* (2013.01); *A61B 2017/00017* (2013.01); *A61B 2017/0046* (2013.01); *A61B 2017/00345* (2013.01); *A61B 2017/00398* (2013.01); *A61B 2017/00477* (2013.01); *A61B 2017/2919* (2013.01); *A61B 2017/2926* (2013.01); *A61B 2018/00589* (2013.01)

(58) Field of Classification Search
CPC .... A61B 2017/003; A61B 2017/00398; A61B 18/1442; A61B 1/00121; A61B 2017/0046
See application file for complete search history.

(56) References Cited

U.S. PATENT DOCUMENTS

| | | | | |
|---|---|---|---|---|
| 2007/0270784 | A1* | 11/2007 | Smith | A61B 17/068 606/1 |
| 2009/0090763 | A1* | 4/2009 | Zemlok | A61B 90/98 227/175.2 |
| 2011/0065516 | A1* | 3/2011 | Martin | A61B 17/29 464/51 |
| 2011/0174099 | A1* | 7/2011 | Ross | A61B 17/072 74/89.32 |
| 2014/0246471 | A1* | 9/2014 | Jaworek | A61B 17/068 227/175.1 |
| 2014/0263542 | A1* | 9/2014 | Leimbach | A61B 17/064 227/175.2 |
| 2014/0305988 | A1* | 10/2014 | Boudreaux | A61B 17/068 227/175.3 |
| 2014/0305990 | A1* | 10/2014 | Shelton, IV | A61B 17/0686 227/176.1 |
| 2014/0352463 | A1* | 12/2014 | Parihar | F16H 19/02 74/25 |
| 2016/0015408 | A1* | 1/2016 | Sakaguchi | A61B 18/1445 606/34 |

FOREIGN PATENT DOCUMENTS

| | | |
|---|---|---|
| EP | 2777561 A1 | 9/2014 |
| EP | 2837340 A1 | 2/2015 |
| EP | 2837341 A1 | 2/2015 |
| EP | 2837354 A1 | 2/2015 |
| WO | 2013143563 A1 | 10/2013 |
| WO | 2014162495 A1 | 10/2014 |

* cited by examiner

MICROSURGICAL INSTRUMENT, HANDLE AND ENGINE BLOCK FOR A MICROSURGICAL INSTRUMENT

TECHNICAL FIELD

The following invention relates to a microsurgical instrument and to a handle as well as an engine block for the microsurgical instrument.

BACKGROUND

Minimally invasive surgical methods are familiar, as are the instruments they employ, in which at least one degree of freedom is actuated by the motor, offering the advantage that, by selecting an appropriate motor, e.g. a stepper motor, as well as a suitable transmission ratio, it is possible to obtain very well-measured and fine-tuned movements of the work piece (that is, the inserted part being worked with), so that the impacts of unintentional hand movements or tremors can be reduced.

Currently used microsurgical instruments, for example for laparoscopy, consist as a rule of a work piece with a shaft and a scissors or forceps type of working device on its distal end and with a handle by which the degrees of freedom of the working device are controlled. As a result, the work pieces, for example, offer the degrees of freedom of opening/closing of the members of the working device, rotation about the longitudinal axis and pivoting of at least a longitudinal portion of the shaft. It is possible to operate individual functions, or all functions, by motorized power.

Patent EP 2 837 354 A1 discloses a microsurgical instrument in which a distal shaft section is pivoted by means of an electric motor in the handle, which drives a bevel gear. On a secondary shaft powered by the drive bevel on the output side, a spur gear is mounted non-rotatably and engages in two toothed racks. Upon rotation of the spur gear, the one toothed rack moves forward and the other backward. One half-shaft is in turn connected to each of the toothed racks, so that the two half-shafts together are conducted in an outer shaft, which extends to the working device. The half-shafts extend to the anglable distal end and serve as a power transmission element for the angulation.

The electric motor there takes the form of a separate component and can be coupled with the handle only if the toothed wheels of the engine output shaft and the input shaft of the handle are situated at an appropriate angle to one another. For this reason, to couple the motor, if necessary the distally anglable portion must be deflected by hand and the toothed wheels thus brought into an engaged position. As soon as the toothed wheels are engaged, the electric contact is established, and contacts on the engine block and on the base body of the handle are connected through the installation movement of the engine block.

SUMMARY

On the basis of the prior art, it is the object of the present invention to provide a microsurgical instrument that is distinguished by a simplified coupling of the engine block and handle.

This object is fulfilled by a microsurgical instrument according to the invention.

It is an additional object of the invention to provide a handle that can be coupled in simple manner with an engine block and constitutes with it a microsurgical instrument.

The final object of the invention is to provide an engine block that can be coupled with a handle in an easy and time-saving manner in order to constitute a microsurgical instrument.

The inventive microsurgical instrument compromises a handle and an engine block that can be removably installed in the handle. The handle can be coupled with a work piece and, in a first embodiment, comprises a base body and an input shaft mounted in the base body. The input shaft is intended for motorized actuation of at least one degree of freedom of the work piece. The handle comprises, in addition, an engine interface into which the engine block can be installed, so that one or more electric contacts and a mechanical coupling are present on the engine interface. The mechanical coupling comprises a claw coupling element, which is connected non-rotatably with the input shaft and with which a corresponding claw coupling element of the engine block can be coupled. In addition, the handle also has at least one actuation element with which a flow of current can be activated and deactivated through the electric contact of the engine interface in order to operate the engine block when it is installed into the engine interface, According to the invention, the claw coupling element of the handle is mounted on the input shaft so that it can slide longitudinally.

"Work piece," that is, the inserted part being worked with, is understood here to mean the part of a microsurgical instrument that comprises the shaft and the jaw-shaped working device on the distal end (scissors, gripping members, needle holder or the like). The work piece, in addition, can include one or more force or torque transmission means, which run inside the shaft and with which an actuation force can be exerted by the handle to the distal working device. The work piece is coupled with the handle in order to obtain a usable microsurgical instrument.

The members of the working device can each comprise an active portion in their distal end areas; preferably a blade or a gripping surface; the work piece therefore, depending on the configuration of the active portions; can take the form for example of a needle holder, gripping forceps; scissors, biopsy forceps, spreading forceps or dissection forceps. It is possible here that one of the members is fixed and the other member is movable or that both members are movable and are mounted for pivoting in a separate base of the working device.

The longitudinal slidable capacity of the claw coupling element of the mechanical coupling of the handle as foreseen by the invention has the result that the engine block can be coupled not only when the particular claw extensions and spaces between claw extensions of the handle and engine block are situated to fit at an angle with one another, that is, in such a way that they can be interlocked into one another, but also in the angle positions in which the claw extensions impede one another. The claw coupling element of the handle is then simply slid on the input shaft upon coupling or sliding the engine block into the engine interface as far as the corresponding sliding pathway that corresponds to the insertion depth of the claw extensions. The engine block here is advantageously already connected with the electric contact of the engine interface, so that this contact can be rotated by the actuation element of the handle in order to align the claw coupling elements of the mechanical coupling of the handle and of the engine block with respect to their rotation angle in such a way that they can be brought into engagement.

The claw coupling element of the handle can comprise, for instance, a rotation-symmetrical or sleeve-like base body, which can be conducted on the input shaft and from which the claw extensions extend The term "claw coupling element" is intended herein to mean that this is nota matter of a complete claw coupling but rather of a part of it, which forms a complete coupling only in interaction with the respective other part; to that extent a "claw coupling element" is a single coupling jaw.

"Engine block" as used herein does not mean an engine block in the sense of a base motor, but rather the totality consisting of an engine housing, which comprises the force direction structures for installation of the actual engine, junctions, etc., the actual (electric) motor, locking elements for binding to the handle and possible guide bodies for insertion in a guide track of the engine interface of the handle, and so on. The definition of the width of the claw extensions here corresponds to the definition given above.

The handle can be configured, for example, as a pistol grip or pinch grip, while the actuating element can be present, for instance, in the form of a pushbutton; lever or the like.

The base body as defined by the invention must not necessarily be a single piece, but instead can be composed of a number of components.

The engine block and handle in a coupled position form the inventive microsurgical instrument; both the inventive handle and the inventive engine block can, however, be manufactured and mounted separately. Thus, the one of the two that is defective, or needs to be replaced for other reasons, can advantageously be simply exchanged.

In an additional embodiment, the claw coupling element of the handle can comprise claw extensions distributed peripherally, which extend in the longitudinal direction. It is possible, for example, for there to be three or more claw extension that are distributed peripherally at equal angle distances. Advantageously the claw extension taper in thickness toward their free ends that point toward the engine interface.

"Thickness" here is to be understood as peripheral or tangential stretching of the claw extensions, that is, almost in the sense of face width. The taperings here serve as lead-in chamfers which simplify insertion of the claw extensions of the claw coupling element of the engine block that is to be coupled on.

The longitudinal direction here refers to the longitudinal axis of the input shaft on which the claw coupling element is slidably mounted.

In yet another embodiment, a pressure spring element can be positioned between the base body of the handle and an end of the claw coupling element of the mechanical coupling of the handle facing away from the engine interface, so that the input shaft advantageously can be conducted through the pressure spring element for a special economy of construction space.

The pressure spring element can be, for example, a screw-in spring, although it is not excluded to use other pressure spring elements, such as rubber rings, air springs or the like. The term "end" is again to be understood in relation to the longitudinal direction of the input shaft. The pressure spring element holds the claw coupling element in its resting or coupled position; it is slid against the spring force only on coupling of the engine block, in case the claw extensions of the claw coupling elements of the engine block and of the mechanical coupling "overlap" one another or block one another. To prevent the claw coupling element from being pushed from the input shaft by the spring pressure, a safeguard can be provided, for example, a securing bolt screwed into the front surface of the input shaft.

In addition, a friction washer can be provided between the pressure spring element and the claw coupling element.

Advantageously, a friction washer can be provided both between the pressure spring element and the claw coupling element, and between the pressure spring element and the base body. The friction washer(s) may consist of a material that comprises the lowest possible slide friction coefficient in friction pairing with the surfaces of the pressure spring element and of the claw coupling element, for example of a synthetic material like PTFE or a polyamide.

The term "surfaces" herein refers to at least the surfaces coming into contact, that is, for the pressure spring at least the upper or lower spring coil and for the claw coupling element the surface of the end facing away from the engine interface, on which the spring force engages. The friction washers, which serve the function of friction reduction washers, are intended, when the input shaft as well as the claw coupling element conducted on it are rotated, to prevent the spring element from uncontrollably rotating with them and from thereby causing wear. It is useful to install a friction washer, at least between the claw coupling element and the spring element, because this is where the relative motion occurs; in addition, the friction washer acts as a spring cap, which applies the spring force uniformly into the claw coupling element.

According to yet another embodiment, the mechanical coupling of the handle can comprise a coupling housing that is connected with the base body of the handle and in which the claw coupling element of the mechanical coupling of the handle is enclosed. The coupling housing, on a free end facing the engine interface, comprises an opening through which a predetermined claw coupling element of the engine block can be installed, and thus the opening in its shape and dimensions is to be tailored to the predetermined claw coupling element of the engine. It is possible, in addition, for the pressure spring element to be supported on an end of the coupling housing facing away from the opening.

The coupling housing here serves as a protective device for the claw coupling element; that is, it acts almost as a coupling bell. The coupling housing can be connected with the base body by any means deemed appropriate by the practitioner; alternatively, the coupling housing can also be configured as a single unit with the base body; for example as an injection molding piece.

The coupling housing can have, for example, a hollow cylindrical shape, such as an essentially circular-cylindrical shape. At its free end it can comprise an outer edge that is rounded, tapered or chamfered. The longitudinal axis of the coupling housing then is advantageously aligned with the longitudinal axis of the input shaft.

The rounded, tapered or chamfered outer edge serves as a lead-in aid for the engine block; for example, an engine block lead-in sleeve, in which the engine block's claw coupling element is situated, can be slid over it comfortably. The "free end" of the coupling housing refers to the end with the opening, that is, the side pointing to the engine interface, the starting point for inserting the engine's claw coupling element.

In another embodiment the coupling housing can comprise at least one recess on its sheath surface, for example three or even more recesses, which are distributed around the periphery of the coupling housing. The recesses can, in particular, be situated in an area of the claw coupling element.

The "area" refers here to the fact that the claw coupling element is situated within it, that is, the recesses are situated on a longitudinal axial position of the claw coupling element in which the claw coupling element, for example, happens to be in a resting or coupled position.

By means of the recesses the interior of the coupling housing can be cleaned and they can be used to lock the engine block in the coupled position, since it can be arranged for locking elements of the engine block to engage in the recesses.

According to a preferred embodiment, the claw coupling element of the mechanical coupling of the handle can be connected with the input shaft by a form-locked shaft-hub connection. Here the input shaft can comprise an outer profile, such as a spline shaft profile, polygonal profile or one or more flattenings that advantageously extend along a predetermined sliding path of the claw coupling element. The claw coupling element has an internal profile that corresponds with the external profile of the input shaft and with which it is engaged with the external profile. The longitudinally extending external profile of the input shaft makes possible a non-rotatable coupling of the claw coupling element with the input shaft over the complete sliding pathway. The profile shapes mentioned here are merely examples; in addition, it is possible for two or more flattenings to be provided that are distributed peripherally. Alternatively or in addition, one or more tappet elements can be used.

In addition, the handle can comprise a gear unit, in particular a bevel gear comprising an input bevel gear powered by the input shaft and an output bevel gear that engages with the input bevel gear. The output bevel gear can drive a secondary shaft, which runs preferably perpendicular to the input shaft. The secondary shaft can in turn drive a spur gear, with which two toothed rods on opposite peripheral positions engage; said rods each are in turn connected with force transmission means, for example with two half-shafts that can slide with respect to one another to angle an anglable shaft section of a work piece coupled with the handle. Of course; it is also possible for any other functions of the work piece to be operated by the gear unit; for example opening/closing of the jaw-shaped working device or turning of the working device about the longitudinal axis of the shaft, etc. The transmission ratio can be selected depending on the desired apportioning of the movements to be executed.

In this regard, reference is made to EP 283 734 0 A1, EP 2837 341 A1, EP 283 73 54 A1 and EP 277 75 61 A1, whose entire content is included by citation in the present application.

In addition, the at least one electric contact can be situated in a socket or a plug, either of which comprises a contact housing connected with the base body and at least one contact tongue.

In yet another embodiment, the engine interface can comprise one or more guide rails in which at least one corresponding guide element of the engine block can be conducted. The guide rail can advantageously run with at least one section parallel to the input shaft, such as in an end section facing toward the mechanical coupling. By means of the guide rail(s), which run(s) in the end section parallel to the input shaft, the engine block already upon installation is aligned in such a way that the engine output shaft and the input shaft of the handle can be coupled by the respective claw coupling elements, so that operating errors are avoided as much as possible in this work step.

In addition, the handle can take the form of a handle for an electrosurgical instrument that comprises an electric actuation element by means of which a current flow can be activated and deactivated from a power supply, preferably a HF voltage source, to the work piece. Electrosurgical tools serve to stanch blood by coagulation. The electrosurgical tool can be a monopolar or bipolar instrument, and correspondingly the inventive handle can take the form of a handle for both types.

In addition, the claw coupling element of the engine can be non-rotatably connected with an engine output shaft and can be coupled with the claw coupling element of the mechanical coupling, so that in the coupled position the engine output shaft and input shaft are aligned.

Finally, the claw coupling element of the engine block can comprise peripherally distributed claw extensions, which extend in the longitudinal direction of the engine output shaft, such as two, three or more claw extensions which advantageously are distributed peripherally at equal angle distances. Alternatively, it is also possible that only one claw extension is present on the periphery and furthermore it is also possible with several claw extensions that they are situated on the periphery at different angle distances to one another. In advantageous manner, the claw extensions of the claw coupling element of the engine block can taper in thickness toward their free ends that point toward the claw coupling element of the mechanical coupling. Likewise as the tapering ends of the claw coupling element of the mechanical coupling, the taperings of the claw extensions of the claw coupling element of the engine block serve as lead-in chamfers and thus contribute toward a comfortable coupling.

The inventive handle for a microsurgical instrument can be coupled with a work piece and, in a first embodiment, comprises a base body and an input shaft mounted in the base body. The input shaft is configured for motorized actuation of at least one degree of freedom of the work piece. The handle comprises, in addition, an engine interface into which the engine block can be installed, so that one or more electric contacts and a mechanical coupling are present on the engine interface. The mechanical coupling comprises a claw coupling element, which is connected non-rotatably with the input shaft and with which a corresponding claw coupling element of the engine block can be coupled. In addition, the handle also has at least one actuation element with which a flow of current can be activated and deactivated through the electric contact of the engine interface in order to operate the engine block when it is installed into the engine interface. According to the invention, the claw coupling element of the handle is mounted on the input shaft so that it can slide longitudinally.

The inventive engine block for a microsurgical instrument can be coupled mechanically and electrically with the engine interface of the handle and comprises a claw coupling element, which is connected non-rotatably with an engine output shaft and can be coupled with a claw coupling element of the mechanical coupling of the engine interface of the handle. In addition, it has at least one or more electric connection elements, which can be connected with the electric contact of the handle. The claw coupling element of the engine block comprises peripherally distributed claw extensions, which extend in the longitudinal direction of the engine output shaft and taper in thickness toward their free ends. Alternatively it is possible here that only one claw extension is present on the periphery and additionally it is also possible with several claw extensions that they are positioned on the periphery at different angle distances to one another.

The electric connection element should be selected corresponding to the electric contact of the engine interface of the handle, for example as a matching plug-socket pair. Thanks to the inventive engine block, whose claw coupling element also has tapering claw extensions at its free ends, the coupling of engine block and handle is once again clearly simplified and accelerated.

Both the inventive engine block and the inventive handle can be produced and mounted separately. Handle and engine block in this case each comprise the features of the engine block installed in the inventive microsurgical instrument and of the handle. The inventively simplified coupling ability of handle and engine block is a result of the interaction of the features of the engine block and of the handle.

To couple the engine block with the handle, the procedure is as follows:

a) installation of the engine block into the engine interface, b) sliding of the engine block in the longitudinal direction of the input shaft in a direction pointing to the claw coupling element and thus aa) if the claw extensions of the claw coupling element of the handle angularly overlap the claw extensions of the claw coupling element of the engine block, by bringing into contact the claw extensions of the claw coupling element of the engine block and the claw extensions of the claw coupling element of the handle, sliding the claw coupling element of the handle onto the input shaft of the handle through a predetermined slide pathway that corresponds to an insertion depth of the claw extensions of the claw coupling element of the engine block into the claw coupling element of the handle in a coupling position, and upon inserting the engine block, connecting the electric contacts of the engine interface of the handle with the electric connection element of the engine block, or bb) if the claw extensions of the claw coupling element of the handle are aligned to fit angularly to the spaces between claw extensions of the claw coupling element of the engine block, insertion (corresponding to the predetermined insertion depth) of the claw extensions of the claw coupling element of the handle into the spaces between claw extensions of the claw coupling element of the engine block and vice versa, thereby connecting the electric contact of the handle with the electric connection element of the engine block, and then ending the procedure, c) after step aa) actuation of the actuation element of the handle, thereby releasing a current flow through the electric contact of the engine interface and rotation of the engine output shaft and of the claw coupling element of the engine block and angularly fitting alignment of the claw extensions of the claw coupling element of the engine block to the spaces between claw extensions of the claw coupling element of the handle and vice versa, d) sliding back the claw coupling element of the handle on the input shaft over the predetermined sliding route, so that the claw extensions of the claw coupling element of the engine block are inserted along the predetermined insertion depth into the spaces between claw extensions of the claw coupling element of the handle.

The term "angularly overlapping" herein refers to the fact that the claw extensions of the engine block or handle are not aligned to fit in the sense that they can engage into the respective spaces between claw extensions, but instead they impede one another. "Angularly overlapping," on the other hand, means an angle position suited for coupling. In coupling, basically two cases are possible: Either the claw extensions of the claw coupling element of the engine block are already aligned with respect to their angle of rotation in such a way that their claw extensions can be inserted into the spaces between claw extensions of the claw coupling element of the mechanical coupling or not. In the second case, the inventive procedure now offers a comfortable possibility for coupling without, for example, requiring manual deflection of a work piece coupled with the handle. To that extent the inventive procedure makes possible a comfortable, rapid and easy coupling of the engine block.

Finally, in step aa) upon sliding the claw coupling element of the handle onto the input shaft, the pressure spring element can be pre-tensed and in step d) the claw coupling element of the handle can be pushed back again by spring weighting by the pressure spring element. In the process, the tapering ends of the claw extensions of the claw coupling element of the engine block slide on the tapering ends of the claw extensions of the claw coupling element of the handle and vice versa, even before the claw extensions of the claw coupling element of the engine block and of the claw coupling element of the handle are aligned to angularly fit the respective corresponding spaces between claw extensions.

These and other advantages are presented by the following description with reference to the accompanying drawings. References to the drawings in the description serve to support the description and to clarify the object. Objects or parts of objects that are essentially identical or similar can be labeled with the same reference numbers. The drawings are merely schematic depictions of embodiments of the invention.

DETAILED DESCRIPTION

Figure 1:
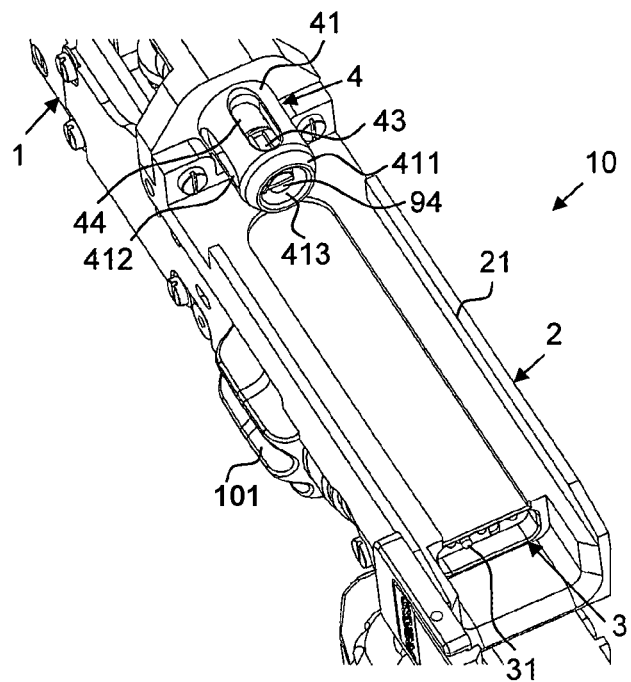
FIG. 1 shows a perspective view of a part of the handle without the engine block.
Figure 7:
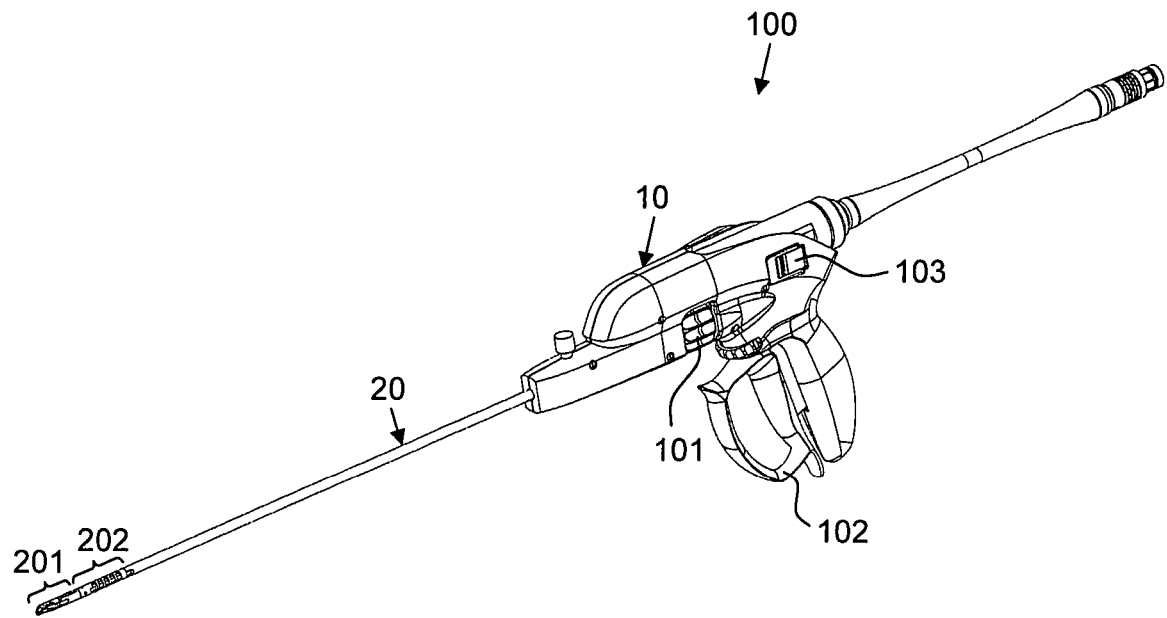
FIG. 7 shows a perspective view of the microsurgical instrument.

The inventive handle 10, which is illustrated in FIG. 1 without engine block 5 (see FIGS. 3 to 6), is intended to be coupled with a work piece 20 for a microsurgical instrument 100 (see FIG. 7). A work piece in this context consists of a shaft that is coupled with the handle 10 and has on its distal end a scissors- or forceps-shaped working device 201, for instance. The functions of the distal working device are controlled by the handle 10, for which purpose the handle 10 has actuation elements. The handle 10 includes a first manual actuation element 101 by which the working device 201 can be rotated about the longitudinal axis of the shaft.

The inventive handle 10 is a motorized handle 10, that is, at least one degree of freedom of the work piece is not actuated manually but rather by an engine. To be able to couple the engine block, the handle 10 has an engine interface 2, on which electric contacts 3 and a mechanical coupling 4 are situated. The engine block 5 (see FIG. 3, for example) is installed for coupling into the guide track 21 and is pushed forward in the longitudinal direction until the contact blades 31 contact a corresponding electric connection element of the engine block and an engine output shaft is connected with the mechanical coupling 4. The mechanical coupling 4 is accompanied by a coupling housing 41, which includes a tapering or chamfering 411 at its end facing the engine interface 2. This chamfering 411 serves as a lead-in aid for a predetermined engine block or more precisely a guide sleeve 51 (see FIG. 3), which is pushed into a coupling position by the coupling housing 41. The sheath surface of the coupling housing 41 bears peripherally distributed recesses 412, which serve for the cleaning of the mechanical coupling 4: In general it would also be possible for the engine block to be locked in these recesses. The guide sleeve 51 of the engine block also comprises recesses 511. Situated in the coupling housing 41 is a claw coupling element 43, which is connected non-rotatably with an input shaft 9 (see FIG. 2).

The claw coupling element 43 is a sleeve-shaped body, which is situated on the input shaft 9 in non-rotatable manner but capable of sliding longitudinally and which has claw extensions 431 (see FIG. 5) pointed toward the engine interface 2 and extending in the longitudinal direction. To prevent the claw coupling element 43 from slipping out of the input shaft 9, a securing bolt 94 is provided, whose head diameter is greater than the inner diameter of the claw coupling element 43. The connection of the claw coupling element 43 and the input shaft 9 is provided by a form-fitting shaft-hub connection, namely a flattening 91 on the outer cross-section of the input shaft 9 and a corresponding inner shape on the inner cross-section of the claw coupling element 43. To allow the claw coupling element 43 to be slid in the longitudinal direction of the input shaft 9, the flattening 91 extends over a predetermined length, which determines and restricts the possible sliding pathway.

Together with a corresponding claw coupling element 53 of the engine block 5 (see FIG. 4), the result then is a complete claw coupling by which the engine moment can be transmitted to the input shaft 9. The corresponding claw coupling element 53 of the engine block 5 can be inserted through the opening 413 of the coupling housing 41 (see FIG. 1) and brought into engagement with the claw coupling element 43.

Figure 2:
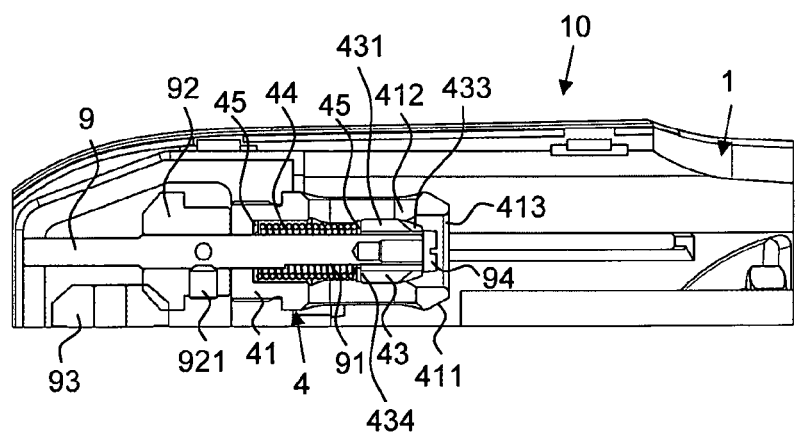
FIG. 2 shows a longitudinal section of a part of the handle without the engine block.
Figure 4:
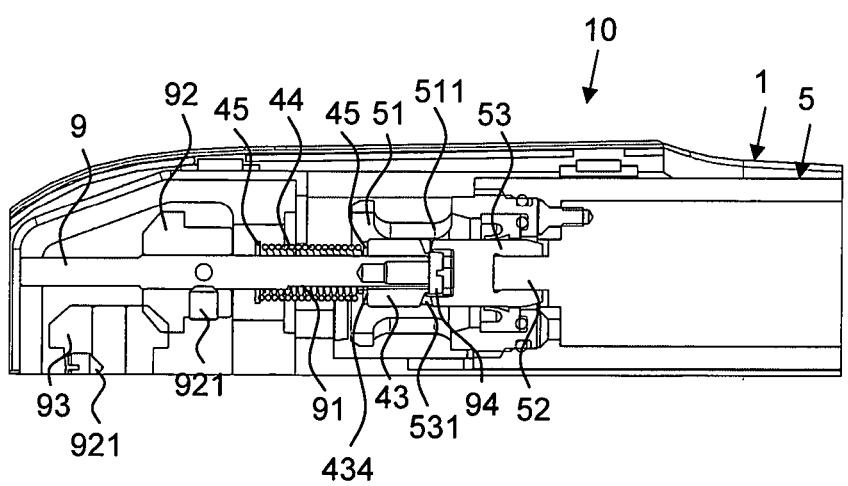
FIG. 4 shows a longitudinal section of a part of the handle with the engine block.

Between an end 434 of the claw coupling element 43 that faces away from the tapering ends 433 of the claw extensions 431 of the claw coupling element 43 and an end of the coupling housing 41 facing away from the opening 413, a pressure spring 44 is situated, through which the input shaft 9 is conducted, as can be seen in FIGS. 2 and 4. The pressure spring 44 is supported at one end on the end of the coupling housing 41 facing away from the opening 413 and at the other end on the end 434 of the claw coupling element 43. The pressure spring 44 provides a longitudinal-axis resting position of the claw coupling element 43, corresponding to the coupling position with the corresponding claw coupling element 53 of the engine block 5 (see FIG. 4). Because the claw coupling element 43 as well as the input shaft 9 are moving parts with respect to the base body 1, the coupling housing 41 and the pressure spring 44, friction washers 45 are provided between an end of the pressure spring 44 pointing to the claw coupling element 43 and an end of the gear unit housing 41 turned away from the opening 413. The aforesaid friction washers 45 serve to reduce friction and consist of a material or have the surface quality that has the lowest possible sliding friction coefficient in a friction pairing with the surfaces of the pressure spring 44 and the claw coupling element 43, for example a synthetic such as a polyamide or PTFE.

The input shaft 9 is mounted in the base body 1 of the handle 10 in an appropriate manner, such as by means of a friction bearing. As shown in FIGS. 2 and 4, in addition, on the input shaft 9, on the input gear side, a bevel gear 92 is secured non-rotatably by a set screw 921, and serves to power a perpendicular-positioned bevel gear 93, which in turn is secured non-rotatably on a secondary shaft.

Because of the alignment of the secondary shaft perpendicular to the longitudinal direction of the shaft of a work piece, it is possible with the inventive handle 10 to produce especially advantageously a snapping motion of the shaft of the work piece via the engine input gear; this is not illustrated, however. For example, on an end of the secondary shaft facing away from the bevel gear 93 on the output gear side, a spur gear can be provided that engages at two opposite peripheral positions with two toothed rods aligned in the longitudinal direction of the shaft of the work piece. By means of these toothed rods, which move in opposite directions in a rotating motion of the spur gear, half-shafts can then be powered, for example, which are conducted in an outer shaft of the work piece and transmit the actuation forces to a snappable shaft section.

Figure 3:
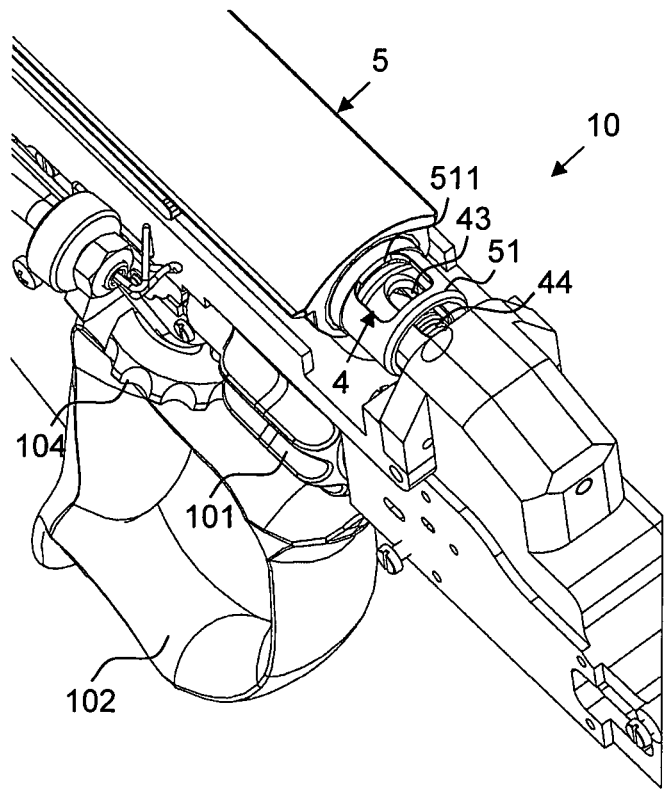
FIG. 3 shows a perspective view of a part of the handle with the engine block.

FIGS. 3 and 4 show the handle 10 with engine block 5 coupled to it. In the illustrated handle 10, this involves a handle 10 with a pistol grip 102 configured as actuation element, said handle having an additional manual actuation element 104 besides the first manual actuation element 101 for rotating the working device about the longitudinal axis. The guide sleeve 51 of the engine block 5 is pushed over the coupling housing 41, so that the engine block is spatially secured with respect to the mechanical coupling 4 of the handle 10. In FIG. 4, however, the coupling housing 41 (see FIGS. 1 and 2) is blanked out to make its contained components more visible. The claw coupling element 53 of the engine block 5 is non-rotatably connected with the engine output shaft 52 and has peripherally distributed claw extensions 531, which in coupling position engage in the spaces between claw extensions of the claw coupling element 43 and thus produce the form-fit connection to transmit torque. The pressure spring 44 is lengthened because the coupling is in coupling position, and the claw coupling element 43 of the handle is contiguous with the securing screw 94.

Figure 5:
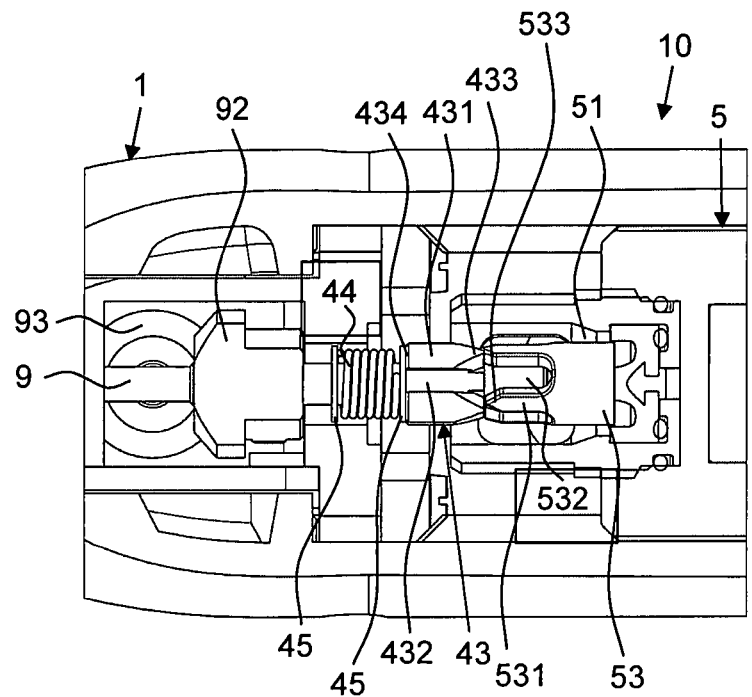
FIG. 5 shows an overhead view of a part of the handle with uncoupled claw coupling elements.
Figure 6:
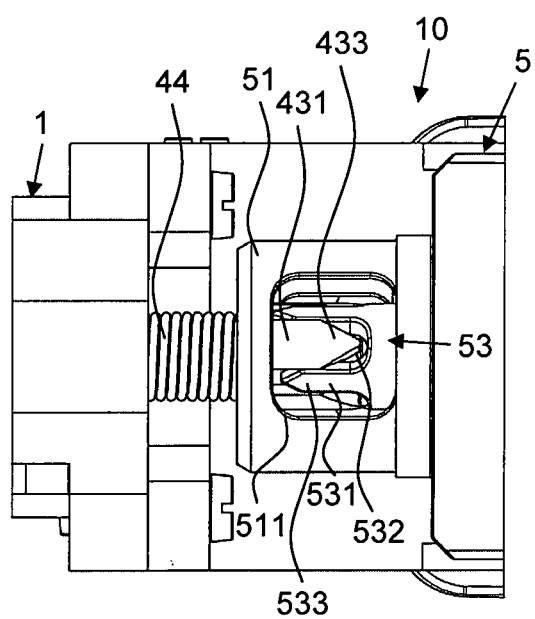
FIG. 6 shows an overhead view of a part of the handle with coupled claw coupling elements.

On coupling the engine block 5 with the base body 1 of the handle 10, two cases can occur: Either the claw coupling elements 43, 53 of the mechanical coupling 4 and of the engine block 5 are oriented to fit one another in the sense that the respective claw extensions 431, 531 can engage in the corresponding spaces between claw extensions 432, 532, or they are not oriented to fit. In the first case the claw extensions 531 of the engine block 5, upon installation of the engine block into the engine interface 2 or more precisely between the guide tracks 21 (see FIG. 1), will engage in the spaces between claw extensions 432 of the claw coupling element 43 of the mechanical coupling 4 of the handle 10; in the other case this is not possible because the respective claw extensions 431, 531 overlap one another; that is, impede one another; this is illustrated in FIG. 5.

So far it was not possible to rotate the engine output shaft 52 by actuating the actuation element, because the electric coupling of the engine block 5 was possible only in coupling position; that is, if the claw extensions 531 of the claw coupling element 53 of the engine block engage in the spaces between claw extensions 432 of the claw coupling element 43 of the mechanical coupling 4. As a rule, the engine block 5 itself additionally comprises a gear unit with a very high transmission ratio; possibly even a snail wheel stage, so that the engine output shaft also cannot be turned manually because it blocks itself.

So far, then, in order to couple the claw coupling elements 43, 53, the work piece had to be deflected at its snappable end in order to rotate the input shaft 9 indirectly and to align the two claw coupling elements 43, 53 toward each other with respect to their angle of rotation in such a way that they can be brought into engagement with one another; however, this is not only difficult but also has the disadvantage that the sterile working device must be handled.

The inventive handle 10 makes it possible for the engine block 5 to be already electrically connected while the claw coupling elements 43, 53 are not yet engaged. If, upon inserting the engine block 5, the claw extensions 431, 531 are aligned to overlap with one another with respect to their angle of rotation, the claw coupling element 43 of the handle is pushed in the direction of the longitudinal axis by the claw coupling element 53 of the engine block, or more precisely through contact of the respective claw extensions 431, 531; so that the pressure spring 44 is pressed together. In this position, the electric contacts 3 are now connected with the corresponding electric circuit of the engine block 5, so that the engine output shaft 52 can be rotated simply by actuating the actuation element, that is, a simple switch.

Hereafter the tapering ends 433, 533 of the claw coupling elements 43, 53 begin to slide toward one another, which, finally, as soon as the claw extensions 531 of the claw coupling element 53 of the engine block are aligned to fit to the spaces between claw extensions 432 of the claw coupling element of the mechanical coupling 4, has as a result the engaging of the claw extensions 531 of the claw coupling element 53 of the engine block into the spaces between claw extensions 432 of the mechanical coupling 4. The claw coupling element 43 of the mechanical coupling 4 is hereby pushed back into its resting position by the pre-tensed pressure spring 44; this process is made clear by the illustration in FIG. 6.

It is advantageous, when using the inventive handle 10 in coupling the engine 5, to dispense with the step in which the distal snappable shaft section of the work piece must be diverted to couple the engine block 5. As a result, the time required for coupling is considerably reduced and the risk of contamination of the work piece is lowered. The inventive handle therefore makes it possible to increase the surgeon's working efficiency and helps avoid postoperative complications through infection.

FIG. 7, finally, shows an overview of the inventive microsurgical instrument 100. The microsurgical instrument 100 consists essentially of a handle 10 and the coupled-on work piece 20, which in turn consists of the working device 201 and the connecting shaft.

The functions of the work piece 20 can be controlled by means of the handle 10, or more precisely its actuation elements 101, 102, 103. The functions consist here of the following: rotation of the working device 201 about the longitudinal axis of the shaft, opening/closing of the members and angulation of the anglable shaft section 202. The handle 10 has three actuation elements 101, 102, 103, wherein by means of the first (manual) actuation element 101 the working device 201 can be rotated about the longitudinal axis, by means of the second (manual) actuation element 102 the members can be opened and closed, and by means of the actuation element 103, which is an electric actuation element, the current supply to the engine block can be activated.

What is claimed is:

1. A microsurgical instrument, comprising:
   a handle configured to be coupled with a work piece, and
   a removably installable engine block,
   wherein the handle includes:
      a base body,
      an input shaft mounted in the base body, for motorized actuation of at least one degree of freedom of the work piece,
      an engine interface, into which the engine block is configured to be removably installed, and on which at least one electric contact and one mechanical coupling are situated, wherein the mechanical coupling comprises a claw coupling element of the handle that is connected non-rotatably with the input shaft and is configured to be coupled with a corresponding claw coupling element of the engine block,
      at least one actuation element, with which a current flow can be activated and deactivated by the electric contact of the engine interface,
   wherein the claw coupling element of the handle is mounted so that it can be slid lengthwise on the input shaft.

2. The microsurgical instrument according to claim 1, wherein the claw coupling element of the handle comprises on its periphery at least two claw extensions, extending in a longitudinal direction, which are peripherally distributed at equal or different angle distances, whereby the thickness of the claw extensions tapers toward their free ends pointing to the engine interface.

3. The microsurgical instrument according to claim 1, wherein a pressure spring element is positioned between the base body of the handle and an end of the claw coupling element of the handle facing away from the engine interface,
   wherein the input shaft is conducted through the pressure spring element.

4. The microsurgical instrument according to claim 3, wherein a friction washer is positioned between the pressure spring element and the claw coupling element of the handle or one friction washer each is positioned both between the pressure spring element and the claw coupling element of the handle and between the pressure spring element and the base body, each friction washer being made of a material that comprises a low sliding friction coefficient in friction pairing with a surface of the pressure spring element and claw coupling element of the handle.

5. The microsurgical instrument according to claim 3, wherein the mechanical coupling comprises a coupling housing that is connected with the base body and in which the claw coupling element of the handle is enclosed,
   wherein the coupling housing, on a free end facing the engine interface, comprises an opening, through which a predetermined claw coupling element of the engine block can be conducted, and
   wherein the pressure spring element is supported on an end of the coupling housing facing away from the opening.

6. The microsurgical instrument according to claim 5, wherein the coupling housing has a hollow cylindrical shape, and comprises on the free end at least one rounded, tapered, or chamfered outer edge, and wherein a longitudinal axis of the coupling housing and a longitudinal axis of the input shaft are aligned with one another.

7. The microsurgical instrument according to claim 6, wherein the coupling housing on its sheath surface comprises at least one recess which is distributed over a periphery of the coupling housing, wherein the at least one recess is situated in an area of the claw coupling element of the handle.

8. The microsurgical instrument according to claim 1, wherein the claw coupling element of the mechanical coupling of the handle is connected with the input shaft by a form-fitted shaft-hub connection,
wherein the input shaft has an external profile, which is either a spline shaft profile, a polygonal profile, or one or more flattenings that extend along a predetermined sliding pathway of the claw coupling element, and wherein the claw coupling element has an internal profile corresponding with the external profile of the input shaft.

9. The microsurgical instrument according to claim 1, wherein the handle comprises a gear unit, which comprises an input bevel gear powered by the input shaft and an output bevel gear that engages with the input bevel gear and drives a secondary shaft, which runs perpendicular to the input shaft, and/or
the at least one electric contact is situated in a socket or plug, which comprises a contact housing and at least one contact blade, wherein the contact housing is connected with the base body.

10. The microsurgical instrument according to claim 1, wherein the engine interface comprises at least one guide track, in which at least one corresponding guide body of the engine block is conducted, wherein the guide track runs parallel to the input shaft in an end section facing the mechanical coupling.

11. The microsurgical instrument according to claim 1, wherein the microsurgical instrument is an electrosurgical microsurgical instrument and the handle comprises an electric actuation element by which a current flow can be activated and deactivated from a power source to the work piece.

12. The microsurgical instrument according to claim 1, wherein the claw coupling element of the engine block is connected non-rotatably with an engine output shaft and is coupled with the claw coupling element of the handle,
wherein the engine output shaft and the input shaft of the handle are aligned in a coupled position.

13. The microsurgical instrument according to claim 12, wherein the claw coupling element of the engine block comprises on its periphery at least two peripherally distributed claw extensions, which extend in a longitudinal direction of the engine output shaft and are distributed peripherally at equal or different angle distances, wherein the claw extensions taper in thickness toward their free ends that point toward the claw coupling element of the handle.

14. A handle for a microsurgical instrument, wherein the handle is configured to be coupled with a work piece and comprises:
a base body,
an input shaft mounted in the base body and configured for motorized actuation of at least one degree of freedom of the work piece,
an engine interface, into which an engine block is configured to be removably installed, wherein at least an electric contact and a mechanical coupling are present on the engine interface, wherein the mechanical coupling comprises a claw coupling element of the handle, which is connected non-rotatably with the input shaft and with which a corresponding claw coupling element of the engine block is configured to be coupled, and
at least one actuation element, with which a current flow can be activated and deactivated through the electric contact of the engine interface,
wherein the claw coupling element of the handle is mounted so that it can slide longitudinally on the input shaft.

15. The microsurgical instrument according to claim 2, wherein a pressure spring element is positioned between the base body of the handle and an end of the claw coupling element of the handle facing away from the engine interface, wherein the input shaft is preferably conducted through the pressure spring element.

16. The microsurgical instrument according to claim 4, wherein the mechanical coupling comprises a coupling housing that is connected with the base body and in which the claw coupling element of the handle is enclosed,
wherein the coupling housing, on a free end facing the engine interface, comprises an opening, through which a predetermined claw coupling element of the engine block can be conducted, and
wherein the pressure spring element is supported on an end of the coupling housing facing away from the opening.

17. The microsurgical instrument according to claim 1, wherein the claw coupling element of the handle is configured to be slid lengthwise from a semi-coupled position to a fully coupled position when the claw coupling element of the engine block and the claw coupling element of the handle fit together at an angle.

18. The microsurgical instrument according to claim 17, wherein in the semi-coupled position the engine block is electrically connected and the claw coupling element of the engine block and the claw coupling element of the handle are not mechanically connected.

19. The microsurgical instrument according to claim 18, wherein the claw coupling element of the engine block is configured to electrically rotate while in the semi-coupled position to the angle; wherein at the angle the claw coupling element of the handle can be slid lengthwise to the fully coupled position.

* * * * *